United States Patent [19]

Itoh

[11] 4,269,195

[45] May 26, 1981

[54] APPARATUS FOR MEASURING A PULMONARY FUNCTION

[75] Inventor: Ayao Itoh, Yokohama, Japan

[73] Assignee: Tokyo Shibaura Denki Kabushiki Kaisha, Kawasaki, Japan

[21] Appl. No.: 41,708

[22] Filed: May 23, 1979

[30] Foreign Application Priority Data

May 31, 1978 [JP] Japan .................................. 53-64290

[51] Int. Cl.³ .............................................. A61B 5/08
[52] U.S. Cl. ..................................... 128/723; 128/734
[58] Field of Search ......... 128/721, 723, 725, 734–735

[56] References Cited

U.S. PATENT DOCUMENTS

| | | | |
|---|---|---|---|
| 3,452,743 | 7/1969 | Rieke | 128/723 |
| 3,882,851 | 5/1975 | Sigworth | 128/723 |
| 4,036,217 | 7/1977 | Ito et al. | 128/723 |
| 4,182,314 | 1/1980 | Boughton | 128/734 |

FOREIGN PATENT DOCUMENTS 1908472  7/1977  Fed. Rep. of Germany ........... 128/723

OTHER PUBLICATIONS

Barker, A. et al., "Simple Impedance Pneumograph and Volume Integrator", Mod. & Biol. Engr., vol. 11, No. 3, May 1973.
Geddes, L. A., "The Impedance Pneumograph", Aerospace Medicine, Jan. 1962, pp. 28–33.
Henderson, R. P., "An Impedance Camera for Spatially Specific Measurements of the Thorax", IEEE BME Trans., vol. BME-25, No. 3, May 1978.

*Primary Examiner*—Robert W. Michell
*Assistant Examiner*—Francis J. Jaworski
*Attorney, Agent, or Firm*—Oblon, Fisher, Spivak, McClelland & Maier

[57] ABSTRACT

A plurality of impedance pneumographs for measuring impedances at the locations of a human thorax are provided together with a pneumotachograph for measuring an amount of respiration. An impedance value measured at the inhalation starting point is subtracted from an impedance value measured at other time points to obtain an impedance variation. The impedance variations corresponding to the locations of the thorax are added to obtain a sum of the impedance variations. A ratio of the impedance at each location of the thorax to the sum of the impedance variations is calculated and an amount of ventilation at each location of the thorax is found by the impedance ratio and respiration amount.

7 Claims, 5 Drawing Figures (a) OUTPUT OF PNEUMOTACHOGRAPH 14

(b) OUTPUT OF WAVE SHAPING CIRCUIT 21

(c) OUTPUT A OF MONO· MULTI. 22

(d) OUTPUT B OF MONO· MULTI. 23

(e) OUTPUT Y OF INTEGRATOR 16

(f) OUTPUT OF IMPEDANCE PNEUMOGRAPH (g) OUTPUT OF SAMPLEHOLD CIRCUIT (h) OUTPUT X OF PNEUMONIC AMPLITUDE DETECTOR

APPARATUS FOR MEASURING A PULMONARY FUNCTION

BACKGROUND OF THE INVENTION

This invention relates to an apparatus for measuring a pulmonary function.

Most of the patients admitted to ICU (Intensive Care Unit) sickrooms are post-operative patients. Recently, an increasing number of people with no experience of operation have been admitted as patients to such sickrooms. Most of these patients suffer from acute respiration failure or insufficiency. Various check methods have at present been studied so as to elevate the quality of checking of respiratory diseases or troubles as well as to effect their earlier diagnosis. A pulmonary function checking effected for the ventilating state of the local area of the lungs is among the important checking lists. A conventional pulmonary function checking method includes, for example, a method for checking a respiratory sound or murmur by a stethoscope and method for measuring the state of a radioisotope (i.e. a gasified radioisotope inhaled through the bronchus) distributed in the alveoli of the lungs by an external scintillator and checking the function of ventilation based on the measured data. The former method is easiest and can locally grasp the dynamic state of ventilation for each respiratory movement, but it is difficult to locate the field of the lungs where the respiratory murmur is produced. The latter method, on the other hand, is complicated, since it requires a radioisotope and computer. Furthermore, it is difficult for the operator to check the pulmonary function in the dynamic state with which each respiration occurs.

Recently, an impedance method has been developed which can check a pulmonary function. This method utilizes a principle on which the respiratory electrical impedance of the thorax vary according to a variation in amount of ventilation. An apparatus for checking a pulmonary function by such an impedance method is disclosed in P. Henderson et al., IEEE Transactions on Biomedical Engineering, Vol. BME-25, No. 3, May 1978. This method measures an impedance distribution over the thorax by a matrix array of electrodes on the thorax and displays the impedance distribution on a display device. In this method, however, impedances measured include an impedance resulting from a contact of each electrode with the skin of the thorax. Since the impedance varies due to the contact state of the electrode, it would be difficult to obtain accurate measurement. Further, the amount of ventilation is merely checked from the overall impedance distribution and it would be difficult to accurately obtain a distribution of air with respect to an accurate amount of respiration of the patient.

SUMMARY OF THE INVENTION

It is accordingly the object of this invention to provide an apparatus for accurately checking a pulmonary ventilation function with a simple arrangement. According to this invention, impedance pneumographs for measuring impedances at a plurality of locations of the thorax are provided together with a pneumonic detector for measuring an amount of respiration. The impedance variations of the fields of the lungs resulting from each respiratory movement are found based on the output signals of the impedance pneumographs and pneumatic detector. A ratio of the impedance variation at each field of the lungs to a sum of the impedance variations is calculated and an amount of ventilation at the respective field of the lungs is measured based on this ratio and amount of respiration.

DETAILED DESCRIPTION OF THE INVENTION

Figure 1:
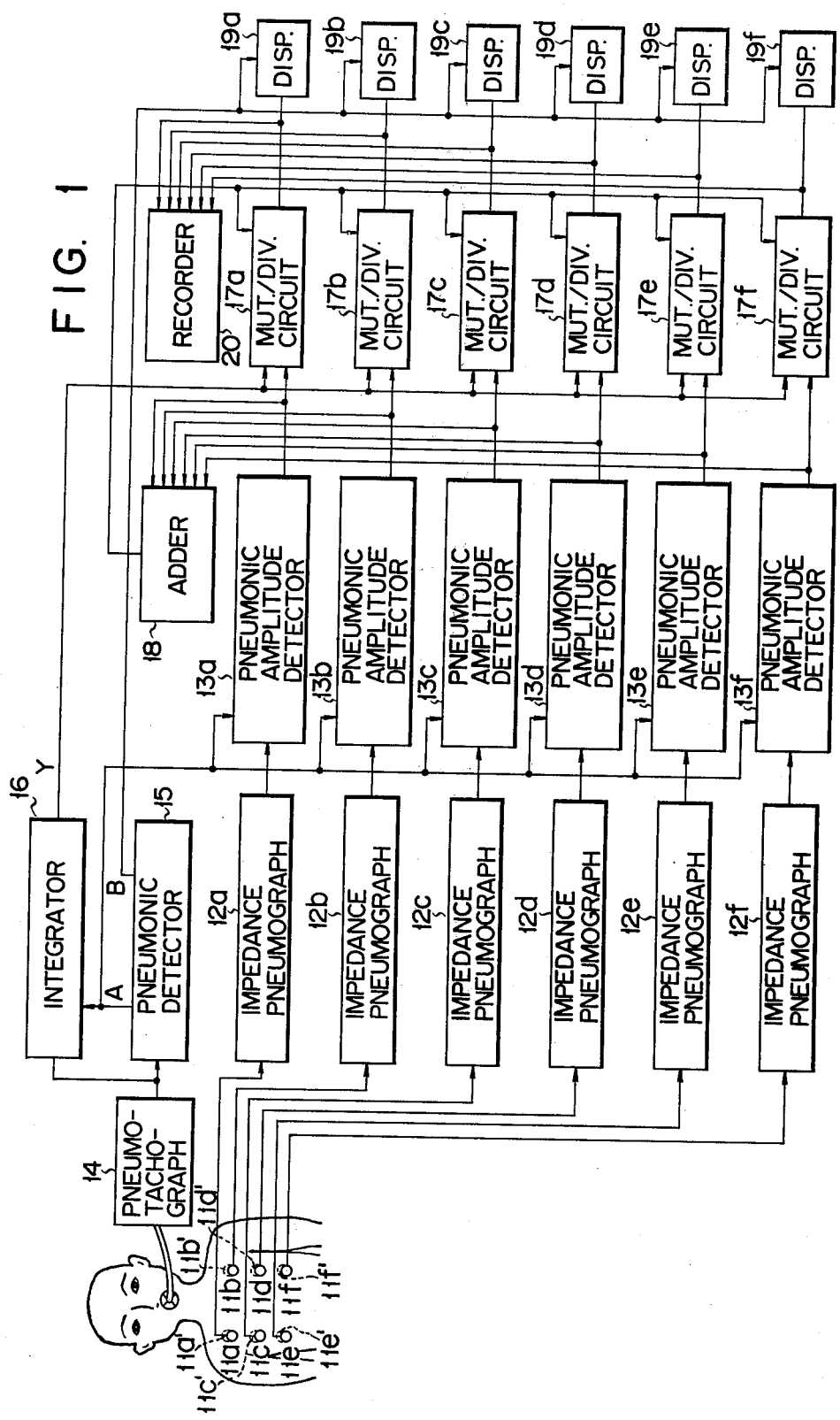
FIG. 1 is a circuit diagram of an apparatus according to the embodiment of this invention.

As shown in FIG. 1, six front electrodes $11a$, $11b$, $11c$, $11d$, $11e$, and $11f$ are attached to the right and left front skin portions of the thorax of a human being while six back electrodes $11a'$, $11b'$, $11c'$, $11d'$, $11e'$ and $11f'$ are attached to the back thereof. Each of the front and back electrodes $11a$ to $11f$ has a current supply electrode element and a voltage detection electrode element. The paired electrodes $11a$, $11a'$, $11b$, $11b'$, $11c$, $11c'$, and $11f$, $11f'$ are connected to the input paired terminals of corresponding impedance pneumographs $12a$ to $12f$ such as, for example, two channel type impedance cardiopulmograph model IPM-02A manufactured by Toshiba. The output terminals of the impedance pneumographs $12a$ to $12f$ are connected to the input terminals of the corresponding pneumonic amplitude detectors $13a$ to $13f$. The output terminal of a tachometer, such as a pneumotachograph 14, for measuring an amount of respiration is connected to the pneumonic detector 15. The pneumonic detector 15 produces output pulses in response to the starting points of inhalation and exhalation, as will be later described. The pulse A outputting terminal of the detector 15 is connected to an integrator 16 and control input terminals of the pneumonic amplitude detectors $13a$ to $13f$. The output terminals of the pneumonic amplitude detectors $13a$ to $13f$ are connected to first input terminals of multiplier/divider circuits $17a$ to $17f$ and the corresponding input terminals of an adder 18. Second input terminals of the multiplier/divider circuits $17a$ to $17f$ are connected to the integrator 16 and third input terminals of the multiplier/divider circuits $17a$ to $17f$ are connected to the adder 18. The output terminals of the multiplier/divider circuits $17a$ to $17f$ are connected to the input terminals of display devices $19a$ to $19f$ and input terminals of a recorder 20.

Figure 2:
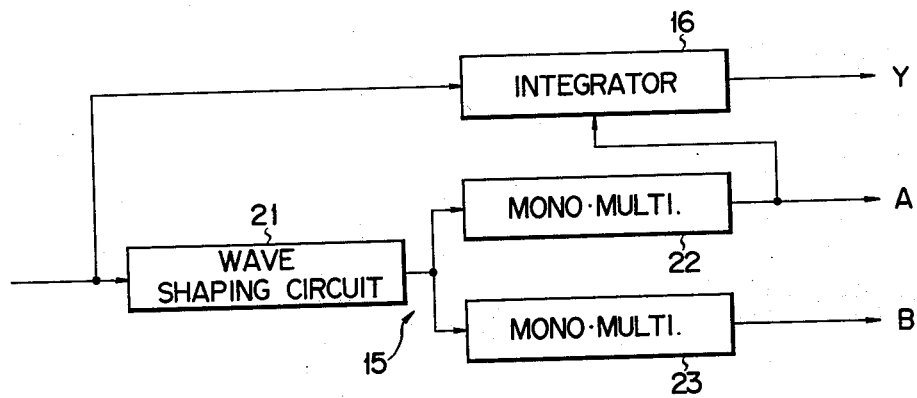
FIG. 2 is a circuit diagram of a pneumonic detector in the apparatus of FIG. 1.
Figure 3:
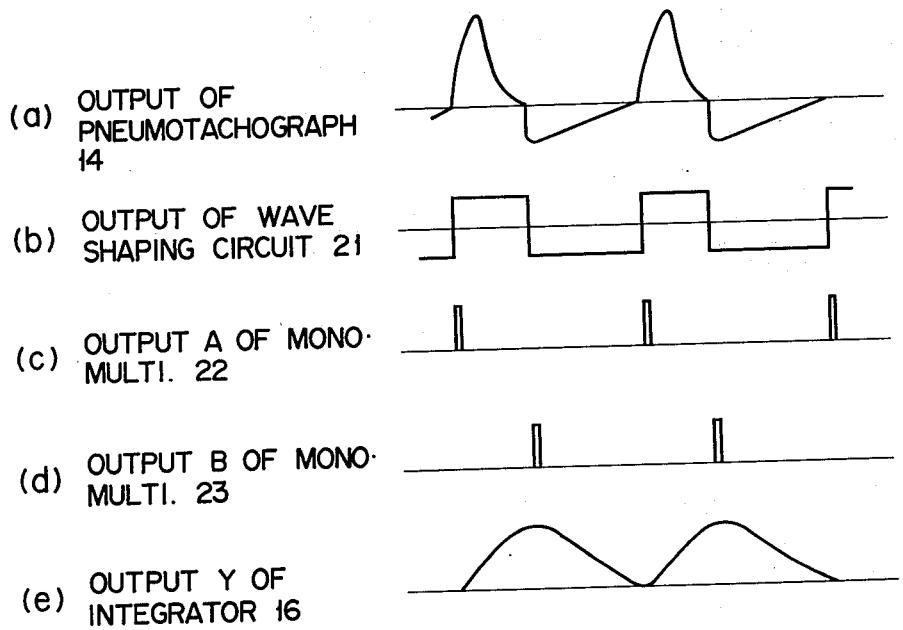
FIG. 3 is a time chart showing the signals of the respective stages of the circuit of FIG. 2.
Figure 4:
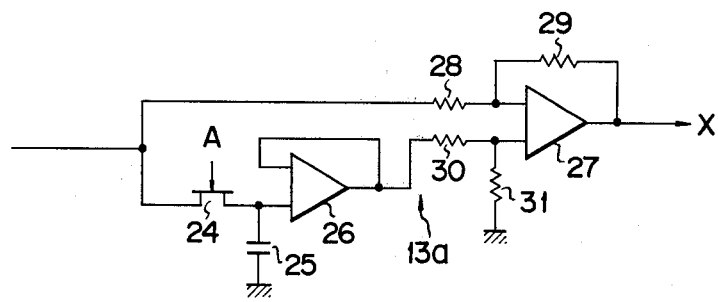
FIG. 4 is a circuit diagram of the pneumonic amplitude detector of the apparatus of FIG. 1.
Figure 5:
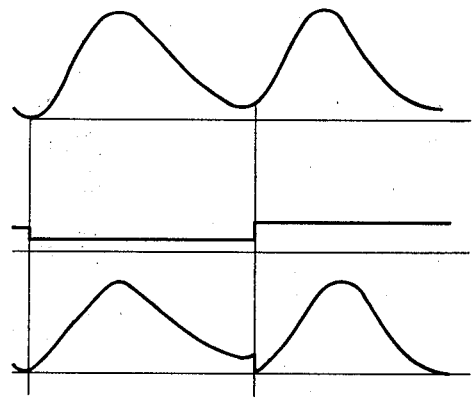
FIG. 5 is a time chart showing the signal of each part of the circuit of FIG. 4.

With the apparatus having such circuit arrangement, the impedances of the six locations of the thorax are measured by the impedance pneumographs $12a$ to $12f$ and at the same time the amount of respiration is measured by the pneumograph 14. A signal corresponding to the respiration is supplied from the pneumotachograph 14 to the pneumonic detector 15, the arrangement of which is shown in FIG. 2. The output signal of the pneumotachograph 14, i.e. the respiration signal a as shown in FIG. 3 is supplied to a wave shaping circuit 21 and integrator 16 of the detector 15. A wave-shaped signal b as shown in FIG. 3 is outputted from the wave shaping circuit 21 and supplied to monostable multivibrators 22 and 23 of the detector 15. The monostable multivibrator 22 produces an output signal c, i.e. an inhalation starting point pulse signal A in response to the rising-up portion of the signal b and the monostable multivibrator 23 produces an output signal d i.e. an exhalation starting point pulse signal B in response to the falling portion of the signal b. The integrator 16 is reset by the pulse signal A to integrate the output signal a of the pneumatachograph 14 thereby to produce an integrated signal e, i.e. an inhalation amount signal Y. The output signals of the impedance pneumographs 12a to 12f are supplied to the detectors 13a to 13f, respectively. The pneumonic amplitude detector is constructed as shown in FIG. 4 and samples and holds impedance data at the inhalation starting point in response to the pulse signal A. That is, the pulse signal A is supplied to the gate of a field effect transistor (FET) 24 and an output signal f of the impedance data as shown in FIG. 5 is supplied to the source of FET 24. The pulse signal A is produced at each inhalation starting point as shown in FIG. 3 and in consequence an impedance data signal corresponding to the level at the inhalation starting point is sampled and held at a sample/hold circuit comprising FET 24, capacitor 25 and operational amplifier 26. A sample/hold signal of the sample/hold circuit is indicated as a signal g in FIG. 5. The sample/hold signal g is supplied to a subtracting circuit comprising an operational amplifier 27 and resistors 28, 29, 30 and 31. The subtracting circuit subtracts the sample/hold signal g from the impedance signal a of the impedance pneumograph to produce a signal h i.e. an impedance variation data signal X. In this way, the detectors 13a to 13f produce impedance variation data output signals Xa to Xf. The impedance variation data signals Xa to Xf are supplied to the adder 18 and data Z representing the sum of the impedance variations is produced from the adder 18. The data Z is supplied to the multiplier-divider circuits 17a to 17f. The impedance variation data Xa to Xf of the detectors 13a to 13f and inhalation amount data signal Y of the integrator 16 are supplied to the multiplier/divider circuits 17a to 17f where the data signals Z, Xa to Xf and Y are calculated based on the following equation:

$$\frac{\text{amount of inhalation } (Y) \times \text{impedance variation (each of } Xa \text{ to } Xf) \text{ at each location of the thorax}}{\text{sum } (Z) \text{ of impedance variations } (Xa \text{ to } Xf)}$$

As a result of calculation, data obtained from each of the multiplier/divider circuits 17a to 17f shows an amount of ventilation at each location of the thorax. The ventilation amount data from the multiplier/divider circuits are supplied to display devices 19a to 19f and recorder 20. In response to an exhalation starting point representing pulse signal from the pneumonic detector 15 a corresponding ventilation amount data is represented on each of the display devices 19a to 19f. The waveform corresponding to an amount of inhalation at each location of the thorax is recorded on the recorder 20.

According to this invention the impedances of a plurality of locations of the thorax are measured by a corresponding number of impedance pneumographs and at the same time an amount of respiration is measured by the tachometer such as the pneumotachograph and the impedance variations at a plurality of locations of the lungs corresponding to each respiration are found. The ratio of the impedance variation at each location of the thorax to the sum of the impedance variations is obtained based on the sum of the impedance variations. An amount of ventilation at the field of lungs corresponding to a plurality of locations of the thorax is measured based on the ratio and amount of respiration. According to the apparatus, an accurate amount of ventilation can be measured without involving an error resulting from the contact resistance of the electrode placed at each location of the thorax. Furthermore, the amount of ventilation can be measured at a real time for each respiration and it is possible to always grasp the present state of the patient.

While in the above-mentioned embodiment an amount of ventilation at the inhalation period is measured, it is possible to effect such measurement at both the periods of inhalation and exhalation. If measurement is effected, for example, during the exhalation period, the inhalation starting point pulse A and exhalation starting point pulse B may be used in a reverse way. For the measurement at both the periods of the inhalation and expiration the pneumonic amplitude detectors and display devices are operated in response to one of the pulses A and B. If the inhalation and exhalation starting point pulses A and B are switched alternately, an amount of ventilation at the inhalation and exhalation periods can be alternately measured for each respiration. In the above-mentioned embodiment the amount of ventilation is measured according to an amount of respiration for each respiratory movement and if the amount of ventilation is measured with each amount of respiration fixed, it is possible to examine the pulmonary function more accurately. The relative value of the amount of ventilation at each location of the lungs can be obtained without using the amount of respiration, by finding a ratio of the impedance variation at each location of the lungs to the sum of such impedance variations. The examination of the pulmonary function can be made by such relative value.

Although in the above-mentioned embodiment pneumograph is used as the tachometer for measuring the amount of respiration, an anemometer may also be used.

What is claimed is:

1. An apparatus for measuring a pulmonary function, comprising:

a plurality of paired electrodes adapted for attachment to locations on a human thorax corresponding to the lungs of a human being, each of said paired electrodes including a current supply electrode element and voltage detection electrode element;

means for measuring impedances at the respective locations of the lungs, said means including a constant current source for supplying a constant current to the current supply electrode of each electrode pair;

detecting means coupled to said voltage detection electrode of each of said paired electrodes for detecting impedance variations indicative of respiratory movement from the impedances at the respective locations of the lungs;

sum calculating means for calculating a sum of the impedance variations detected by said detecting means;

ratio calculating means for calculating a ratio of each of the impedance variations to the sum of the impedance variations which is obtained by said sum calculating means; and means for determining the pulmonary function using the ratio data obtained by said ratio calculating means.

2. An apparatus for measuring a pulmonary function, comprising:
- a plurality of paired electrodes adapted for attachment to locations on a human thorax, corresponding to a plurality of fields of the lungs, and with each of said paired electrodes including a current supply electrode element and voltage detection electrode element;
- impedance measuring means connected to the paired electrodes for measuring impedances at the respective locations of the lung fields, said impedance measuring means including a constant current source for supplying a constant current to the current supply electrode of each electrode pair;
- detecting means coupled to said voltage detection electrode of each of said paired electrodes for detecting impedance variations indicative of respiratory movement from impedance data representing those impedances at the respective lung fields which are measured by the impedance measuring means;
- sum calculating means for calculating a sum of impedance variations detected by said detecting means;
- respiration measuring means for measuring a volume of respiration from the lungs; and
- ventilation volume calculating means for calculating a volume of ventilation at each of the fields of the lungs from the volume of respiration measured by said respiration measuring means and sum of the impedance variations obtained by said sum calculating means and each of the impedance variations.

3. An apparatus according to claim 2 in which said impedance measuring means comprises a plurality of impedance pneumographs each connected to the corresponding pairs of electrodes.

4. An apparatus according to claim 2 or 3 in which said detecting means comprises signal producing means for producing first and second signals in response to inhalation and exhalation starting points respectively of respiration, and a circuit for subtracting an impedance value at the exhalation starting point from the measured impedance value of said impedance measuring means in response to said first signal of said signal producing means.

5. An apparatus according to claim 2 or 3, further including means for displaying an amount of ventilation obtained by said ventilation amount calculating means.

6. An apparatus according to claim 2 or 3 in which said ventilation amount calculating means comprises circuit means for dividing a product of the value of each of the respective impedance variations and amount of respiration by a sum of the impedance variations.

7. An apparatus according to claim 2 in which said respiration amount measuring means is constructed of a pneumotachograph.

* * * * *